United States Patent
Chhatrala et al.

(10) Patent No.: US 11,285,033 B2
(45) Date of Patent: Mar. 29, 2022

(54) BREATHABLE AND CUSTOMIZED CAST FOR IMMOBILIZATION OF FRACTURED LIMB

(71) Applicant: The Secretary, Department of Biotechnology, New Delhi (IN)

(72) Inventors: Pankaj Kumar K. Chhatrala, Gujarat (IN); Nikhil Kailas Jamdade, Maharashtra (IN); Devanshi Saksena, New Delhi (IN); Bhavuk Garg, New Delhi (IN)

(73) Assignee: THE SECRETARY, DEPARTMENT OF BIOTECHNOLOGY, New Delhi (IN)

( * ) Notice: Subject to any disclaimer, the term of this patent is extended or adjusted under 35 U.S.C. 154(b) by 383 days.

(21) Appl. No.: 15/126,572

(22) PCT Filed: Nov. 6, 2015

(86) PCT No.: PCT/IB2015/058579
§ 371 (c)(1),
(2) Date: Sep. 15, 2016

(87) PCT Pub. No.: WO2016/071873
PCT Pub. Date: May 12, 2016

(65) Prior Publication Data
US 2017/0079830 A1    Mar. 23, 2017

(30) Foreign Application Priority Data
Nov. 8, 2014 (IN) .......................... 3237/DEL/2014

(51) Int. Cl.
*A61F 5/058* (2006.01)
*A61F 5/01* (2006.01)
*A61F 5/04* (2006.01)

(52) U.S. Cl.
CPC .......... *A61F 5/05816* (2013.01); *A61F 5/012* (2013.01); *A61F 5/0118* (2013.01);
(Continued)

(58) Field of Classification Search
CPC ...... A61F 13/04; A61F 5/0118; A61F 5/0102; A61F 5/0111; A61F 5/0113;
(Continued)

(56) References Cited

U.S. PATENT DOCUMENTS 3,110,307 A * 11/1963 Hamilton ................ A61F 13/04
602/8
3,631,854 A * 1/1972 Fryer ....................... A61F 13/04
602/8
(Continued)

FOREIGN PATENT DOCUMENTS

GB   2041758 A    9/1980
WO   2004/100829 A2   11/2004
(Continued)

OTHER PUBLICATIONS

"Epoxy.PDF"—Su, Y-K ; Materials Science and Materials Engineering—Comprehensive Semiconductor Science and Technology: vol. 6, 2011, pp. 28-100; Chapter 6.02: "Nitride-Based LEDs and Superluminescent LEDs"; section 6.02.8.3.1—"Epoxy" (PDF of section 6.02.8.3.1 provided). (Year: 2011).*
(Continued)

*Primary Examiner* — Caitlin A Carreiro
(74) *Attorney, Agent, or Firm* — Mark M. Friedman

(57) ABSTRACT

The present invention provides a breathable orthopedic cast device for immobilizing and stabilizing at least one fractured limb. The breathable orthopedic cast device comprising: a customizable cast member having hollow tubes pre-injected with at least one infusion material, wherein hollow tubes are interlinked with each other to form a mesh structure to
(Continued)

provide breathability to a fractured limb. The breathable orthopedic cast device is a flat unfolded geometry that can be applied by wrapping over an injured body member, or is customized to a shape corresponding to the contours of the body member.

3 Claims, 4 Drawing Sheets

(52) U.S. Cl.
CPC ............... *A61F 5/04* (2013.01); *A61F 5/058* (2013.01); *A61F 5/05858* (2013.01); *A61F 5/05866* (2013.01)

(58) Field of Classification Search
CPC .... A61F 5/0104; A61F 5/0106; A61F 5/0109; A61F 5/41; A61F 5/05816; A61F 5/01; A61F 13/06; A61F 13/061; A61F 13/062; A61F 13/063; A61F 13/064; A61F 13/066; A61F 13/10; A61F 13/107; A61F 13/108; A61F 5/5841; A61F 5/0585; A61F 5/05875; A61F 5/05; A61F 5/02; A61F 5/022; A61F 5/013; A61F 5/0123; A61F 5/0127; A61L 15/07
USPC ...... 602/8, 5, 6, 12, 13, 14, 19–27; 128/887, 128/892, 893
See application file for complete search history.

(56) References Cited

U.S. PATENT DOCUMENTS

| | | | |
|---|---|---|---|
| 3,782,390 A | 1/1974 | Johnson | |
| 3,786,580 A | 1/1974 | Dalebout | |
| 3,990,437 A * | 11/1976 | Boyden, Jr. | A61F 5/04 602/8 |
| 4,385,024 A * | 5/1983 | Tansill | A43B 7/28 264/223 |
| 4,483,332 A * | 11/1984 | Rind | A61L 15/07 602/13 |
| 5,364,693 A * | 11/1994 | Moren | A61L 15/07 442/164 |
| 6,613,006 B1 | 9/2003 | Asherman | |
| 6,673,029 B1 * | 1/2004 | Watson | A61F 13/04 602/6 |
| 7,037,283 B2 * | 5/2006 | Karason | A61F 13/041 602/5 |
| 2008/0319362 A1 * | 12/2008 | Joseph | A61F 5/055 602/7 |
| 2011/0264022 A1 | 10/2011 | Freeman et al. | |
| 2012/0059214 A1 * | 3/2012 | Zhou | A61F 2/2481 600/16 |
| 2013/0102940 A1 | 4/2013 | Joseph | |

FOREIGN PATENT DOCUMENTS

WO 2007/038547 A1 4/2007
WO 2014/071265 A1 5/2014

OTHER PUBLICATIONS

"Definition of Mesh.PDF"—Oxford Languages definition of the term "Mesh" (obtained from www.google.com on Nov. 20, 2020). (Year: 2020).*
Dow Silastic.PDF; accessed from www.Dow.com on Jul. 31, 2021. (Year: 2021).*
International Search Report and Written Opinion for Corresponding International Patent Application No. PCT/B2015/058579, dated Jun. 22, 2016.

* cited by examiner

BREATHABLE AND CUSTOMIZED CAST FOR IMMOBILIZATION OF FRACTURED LIMB

CROSS REFERENCE TO RELATED APPLICATIONS

This application is a National Stage Application of International Application No. PCT/IB2015/058579, filed 6 Nov. 2015, which claims benefit of Serial No. 3237/DEL/2014, filed 8 Nov. 2014 in India and which application(s) are incorporated herein by reference. To the extent appropriate, a claim of priority is made to each of the above disclosed applications.

FIELD OF THE INVENTION

The present invention relates to the field of orthopedic casting systems for immobilizing and supporting fractured body parts.

BACKGROUND AND THE PRIOR ART

Typically, most broken bones of limbs, such as arms and legs, & minor skeletal injuries such as sprains and joint dislocations are immobilized with a cast for support during the healing process. The cast immobilizes the limb to allow the bone fracture to mend itself in proper position. The cast most often used consists of layers of fabric and cotton padding tape wrapped around the limb.

Traditional casts are heavy, uncomfortable, and subject to molding and degradation by water and sweat. This often makes bathing, swimming and other activities difficult and/or impossible for the wearer. Further difficulties may be experienced in the ability for casts to be adjusted to accommodate for swelling. The skin underneath the cast is also subject to irritation, skin breakdown, and pressure points that can lead to infections that can threaten the limb. The technology used in the casting process has changed little in the last 100 years.

Plaster casts were used consistently and devotedly until the 1980's when fiberglass materials became available. The plaster cast suffers with lots of problem as a plaster cast is typically supplied in the form of a casting tape made with a fibrous tape impregnated with plaster of paris or any other stiffening material i.e resin. The plaster is wetted to bond the plaster together to form a hard supporting cast. Once bonded the plaster binds together to make a solid plaster cast with a fabric and cotton padding. The plaster in the casts made in this manner reduces its original strength when it gets wet. Therefore, care must be taken to prevent the cast from getting wet. Additionally, any moisture that gets under the cast wets the fabric and cotton padding tape within the plaster cast. The fabric and cotton padding tape can get wet from washing, bathing, swimming, rain, from perspiration and other such causes. The wet fabric and cotton padding tape causes skin irritation and maceration after a short time. Mildew and bacteria thrive in such an environment and creates an unpleasant odor. Since the plaster cast cannot be wetted, washing and cleaning is very difficult and skin irritants and dirt cannot be washed out.

The plaster cast is also heavy and rigid and it does not allow for swelling and reduction in the limb. The plaster cast most often cannot be made until the swelling in the limb has gone down. If placed before the swelling is reduced, the cast will become too loose and become ineffective in immobilizing the limb. If the cast is placed too early and the limb is still swelling, the cast will become too tight and create pressure. When swelling occurs or continues after the cast has been placed, the cast often has to be split to relieve pressure. Thus, there is a need for such a cast system which allows constant monitoring of the covered part of the injured limb.

The fiberglass cast which is also in use today has some advantages over the plaster cast, but has several problems of its own, in addition to some of the same problems encountered with the plaster cast. The fiberglass cast itself is lighter, air permeable (to some extent), water resistant and more durable than the plaster cast. However, the fabric and cotton padding against the skin may become wet just as in the plaster cast. If this happens, the cast has to be removed to eliminate odors, mildew, and skin irritation just as in the plaster cast. There are few means i.e. hair dryer and like, to dry the cloth padding under the cast once it becomes wet, however such means are cumbersome and are based on nonscientific way(s) and therefore may not be an effective and reliable option. The fiberglass cast is also rigid like the plaster cast. It does not adjust for swelling and body contours to provide a better and more comfortable fit. Thus, there has been felt a need for a casting system which could eliminate the need for padding in it.

There are various products available on the market which are based on POP casting, Fiber glass Casting, Padding materials. Few of them are mentioned below:

For POP Casting
1. Cellona® Plaster of Paris Bandage
2. 3M™ Plaster of Paris Cast B.P (known through
Fiber Glass Casting
1. 3M™ Scotchcast plus casting tape
Padding Materials
1. Aquacast™ padding, Delta-Dry™ waterproof padding
2. Orthoskin™, SPICA SKINZ™

A further major disadvantage of the existing systems is the need for the materials (plaster, fiberglass, Delta-cast) to be immersed in water in order for an exothermic reaction to occur which will activate the hardening or curing process. Plaster or fiberglass splint or cast application requires a systematized set-up of the proper supplies and adequate preparation. This can be messy and inconvenient, and typically results in the cast padding becoming sodden with water which then must dry over time. The temperature of the water affects the length of time necessary for the cast material to cure or harden. Colder water slows the process and requires prolonged pressure or molding of the cast on the patient's extremity, while warmer water will cause the material to set more quickly, produces more heat against the skin, and if the practitioner is not adept at casting may result in hardening prematurely before the layers of cast material have been completely applied or molded. This is at once a messy, time consuming, and often times uncomfortable process for the patient. One can imagine that if one has a fracture of a long bone, such as the tibia, radius, or ulna, that any unnecessary or prolonged manipulation of the extremity will not be appreciated by the patient. Thus, a casting system which does not require water for the hardening or curing process would be highly appreciated. Also, plaster of Paris casts and fibre glass casts are difficult to cut and remove after healing or in case(s) where cast are to be replaced. Also, while cutting plaster dust and fibre dust can cause problems.

WO2004100829 discloses an orthopedic casting article comprising a polymeric foam tape containing one or more curable resins. The polymeric foam tape can be a foam having a substantially open cell structure, substantially closed cell structure, or a substantially reticulated cell structure. The curable resin can be a water-curable resin. The casting article can be multi-layered to obtain an article suitable for splinting applications.

US2011264022 (A1) discloses an orthopedic casting system with a cast tape having a moisture responsive resin therein and a tubular core. The cast tape is wound onto a tubular core for shipment and storage prior to use in forming an orthopedic cast. The tubular core is formed of a flexible polymeric material and includes a wall with an inner and outer surface. The core wall has a plurality of relatively shallow convex and concave portions that extend linearly of the core. When the cast tape is wound on a core, the concave portions provide a series of longitudinal troughs along which water flows adjacent the inner wraps of the cast tape. However, the cast offered by the above applications suffers with the issues of air circulation and washability.

Also, WO2004100829 and US2011264022 describes resin impregnated bandage rolls for cast application. It just improves the cast application process by providing an easy moisturizing bandage roll and easy handling during cast application. The techniques involved in the patent applications do not improve the end result of the cast i.e. washability, mouldability, breathability.

WO2007038547 discloses an orthopedic cast system, comprising a hydrophilic inner layer; a hydrophobic outer layer having opposing surfaces adjacent to said hydrophilic inner layer. The hydrophobic layer has an apparent surface energy less than about 60 dynes per centimeter; and a curable casting material disposed on one of the opposing surfaces.

However, WO2007038547 describes novel material for padding. The Inventor of WO '547 has described a fabric which is resistant to water and so the patient can take a bath or wash the cast. On the contrary, the present invention provides a casting material which does not involve any padding material.

WO2014071265 discloses a multi-layer cast for immobilizing a body member of a patient. The cast of WO '265 comprises a hydrophobic sleeve having a shape configured to be applied over the body member and substantially conform to the shape of the body member; and a moldable layer configured to be positioned around the sleeve and hardened to conform to the shape of said body member adjacent to the sleeve. The moldable layer comprising a network of pores that extend through the moldable layer; wherein the pores are configured to contact the hydrophobic sleeve to promote the flow of moisture from the hydrophobic sleeve outward through the moldable layer.

However, the technology disclosed in WO '265 employs 3 different layers to provide the desired function, which makes the whole cast more difficult and complicated while wearing/casting. Further, WO '265 employs a hydrophobic layer to keep moisture away from skin but the technology is not completely resistant to water. Water may go into the outer layer of the cast which is subsequently dried by evaporation only. On the contrary, the casting material of the present invention is quite simple to be used while wearing/casting.

US2013102940 discloses a unitized cast system for immobilizing and supporting a body part. The unitized casting system includes a first inner layer for padding and dissipating heat against the patient's skin. A second layer is formed from a thermoformable structural material such as perforated plastic. A protective third outer layer is provided to provide insulation for the second layer. These three layers are formed together to form a unitized cast system that is easily formed and applied to the patient.

However, the thermoformable plastic used in US '940 becomes soft at temperatures of 40 to 50 degree centigrade and flowable when the temperature is greater than 60° C. This kind of material is certainly moldable over body parts but its strength is questionable in hot climate areas, hot water baths, or for workers exposed to high temperatures (furnace). Apart from that this kind of cast system is not resistant to water as the thermoformable layer is sandwiched between a heat dissipating layer and an insulating layer which are certainly some kind of fabrics or porous material which may absorb water.

In comparison to the technology disclosed in U.S. Pat. No. '940, the cast system of the present invention is strengthened by thermosetting material which does not degrade in the temperature range of application. Since the casting material of the present invention does not require any padding or fabric, it can be used in wet conditions as well as without any complications.

Reference is made to U.S. Pat. No. 6,613,006B1, wherein casts for immobilizing a human extremity and a method of making the same is disclosed. It discloses a process to apply a first layer (padding) with the material made-up of cellulose so that it will disintegrate when the limb is immersed into water. Casting tape (layer) is made-up of carbon-fiber impregnated with resin and having holes in a 45 or 90 degree configuration with the outer edge. The casting layer is available in roll form and wrapped over a limb like POP tape. In-order to have visibility to skin, Holes in the layers must be aligned to each other. However, after wrapping, the whole limb has to be immersed into liquid (water) in-order to cure the casting layer and remove the first layer.

However, compared to U.S. Pat. No. '006B1, the casting device in the present invention is easy to apply as there is no need to apply a first layer (padding layer), and further it does not require water for curing. Moreover, the casting device of the present invention is a single layered design so there is no need for alignment of holes as in U.S. Pat. No. '006B1. The casting device of the present invention has elastic properties before curing so it has better moldability during application.

Thus, there is a need for a cost effective flexible casting system for immobilizing a body member of a patient, which is lighter in weight, breathable and washable along with having the advantages of being able to be customized according to the need of an individual patient, is capable of maintaining a uniform pressure throughout the covered area and allowing viewing through to the skin to watch for swelling of the covered skin.

OBJECTS OF THE INVENTION

An object of the present invention is to overcome the drawback/disadvantages of the prior art.

Yet another object of the present invention is to provide a flexible casting system which is lighter in weight, breathable and washable.

Yet another object of the present invention is to provide a flexible casting system which can be customized according to an individual's need.

Yet another object of the present invention is to provide a casting system which eliminates the use of padding in it.

Yet another object of the present invention is to provide a casting system which does not require water for the hardening or curing process.

Yet another object of the present invention is to provide a casting system which provides uniform pressure throughout the covered part of skin.

Yet another object of the present invention is to provide a casting system which allows viewing through to the skin to watch for swelling of the covered skin.

Yet another object of the present invention is to provide a casting system which prevents infection of the covered skin.

Yet another object of the present invention is to provide a casting system which allows for maintaining general hygiene.

Still another object of the present invention is to provide a cost effective casting system which comprises all the above technical advantages

SUMMARY OF THE INVENTION

The following presents a simplified summary of the invention in order to provide a basic understanding of some aspects of the invention. This summary is not intended to identify essential features of the claimed subject matter nor is it intended for use in determining or limiting the scope of the claimed subject matter. Its sole purpose is to present some concept of the invention in a simplified form as a prelude to a more detailed description of the invention presented later.

Accordingly, in one implementation, there is provided a breathable orthopedic cast device for immobilizing and stabilizing an injured body member, said breathable orthopedic cast device comprising:
 a customizable cast member having a plurality of hollow tubes interlinked with each other to form a mesh structure and capable of receiving at least one infusion material, said mesh structure configured to provide breathability to said fractured limb and said customizable cast member made of flexible material.

In one implementation, there is provided a method for immobilizing and stabilizing at least one fractured limb by means of a breathable orthopedic cast device, said method comprising:
 casting a customizable cast member having a shape corresponding to a contour of a patient's body member;
 pre-injected/infusing, by an external means, at least one infusion material into said customizable cast member;
 wrapping, said customizable cast member around a fractured limb;
 wearing or securing, by means of a locking member, said customizable cast member around said fracture limb;
 curing, said customizable cast member by unwrapping said polythene layer or allowing the injected infusion material to harden.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taken in conjunction with the accompanying drawings in which.

Persons skilled in the art will appreciate that the elements in the figures are illustrated for simplicity and clarity and may have not been drawn to scale. For example, the dimensions of some of the elements in the figure may be exaggerated relative to other elements to help to improve understanding of various exemplary embodiments of the present disclosure. Throughout the drawings, it should be noted that like reference numbers are used to depict the same or similar elements, features, and structures.

DETAILED DESCRIPTION OF THE PRESENT INVENTION

The following description with reference to the accompanying drawings is provided to assist in a comprehensive understanding of exemplary embodiments of the invention. It includes various specific details to assist in that understanding but these are to be regarded as merely exemplary.

Accordingly, those of ordinary skill in the art will recognize that various changes and modifications of the embodiments described herein can be made without departing from the scope of the invention. In addition, descriptions of well-known functions and constructions are omitted for clarity and conciseness.

The terms and words used in the following description and claims are not limited to the bibliographical meanings but are merely used by the inventor to enable a clear and consistent understanding of the invention. Accordingly, it should be apparent to those skilled in the art that the following description of exemplary embodiments of the present invention are provided for illustration purpose only and not for the purpose of limiting the invention as defined by the appended claims and their equivalents.

It is to be understood that the singular forms "a," "an," and "the" include plural referents unless the context clearly dictates otherwise.

Features that are described and/or illustrated with respect to one embodiment may be used in the same way or in a similar way in one or more other embodiments and/or in combination with or instead of the features of the other embodiments.

It should be emphasized that the term "comprises/comprising" when used in this specification is taken to specify the presence of stated features, integers, steps or components but does not preclude the presence or addition of one or more other features, integers, steps, components or groups thereof.

The objects, advantages and other novel features of the present invention will be apparent to those skilled in the art from the following detailed description when read in conjunction with the accompanying drawings.

Figure 1:
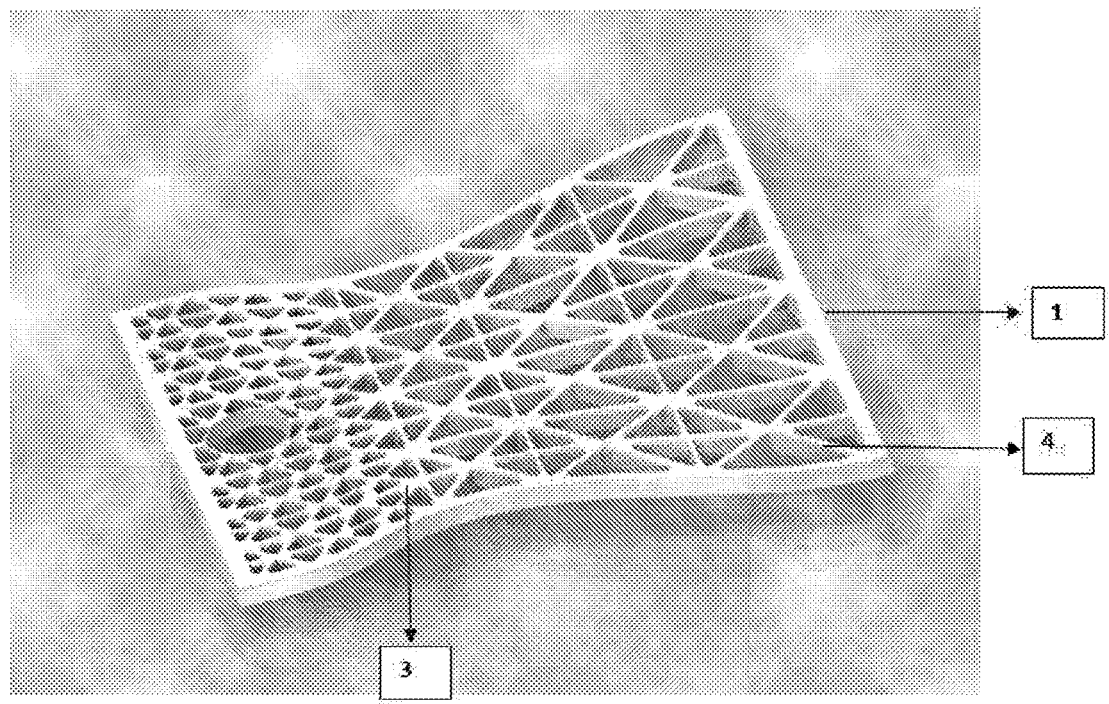
FIG. 1 illustrates a 3-Dimensional view of the flexible cast member before application to a fractured limb, in accordance with an embodiment of the present subject matter.
Figure 2:
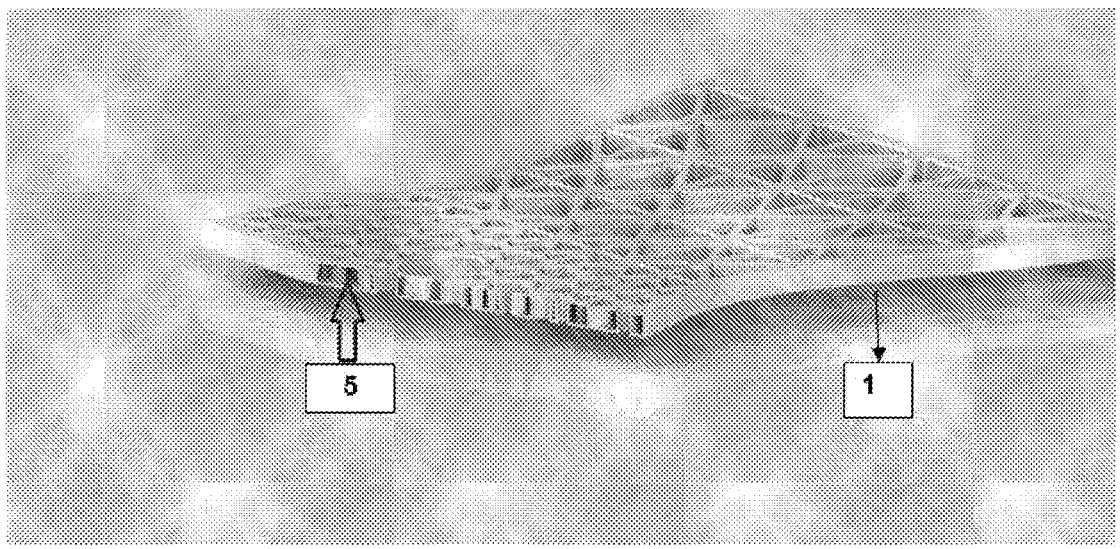
FIG. 2 illustrates the flexible cast member with a cavity to receive infusion material, in accordance with an embodiment of the present subject matter.

In one implementation, as shown in FIG. 1, a 3-Dimensional view shows a flexible cast member (1) before application to a patient's injured body member, wherein the injured body member can be a fractured limb. The flexible cast member comprises: a customizable cast member (1) having a plurality of hollow tubes (4) injected with an infusion material, said hollow tubes interlinked with each other to form a mesh structure (3) to provide breathability to said fractured limb. As shown in FIG. 2, the infusion material can be injected into a cavity or an inlet (5) provided on the surface of the cast member (1), as shown in FIG. 2.

Figure 3:
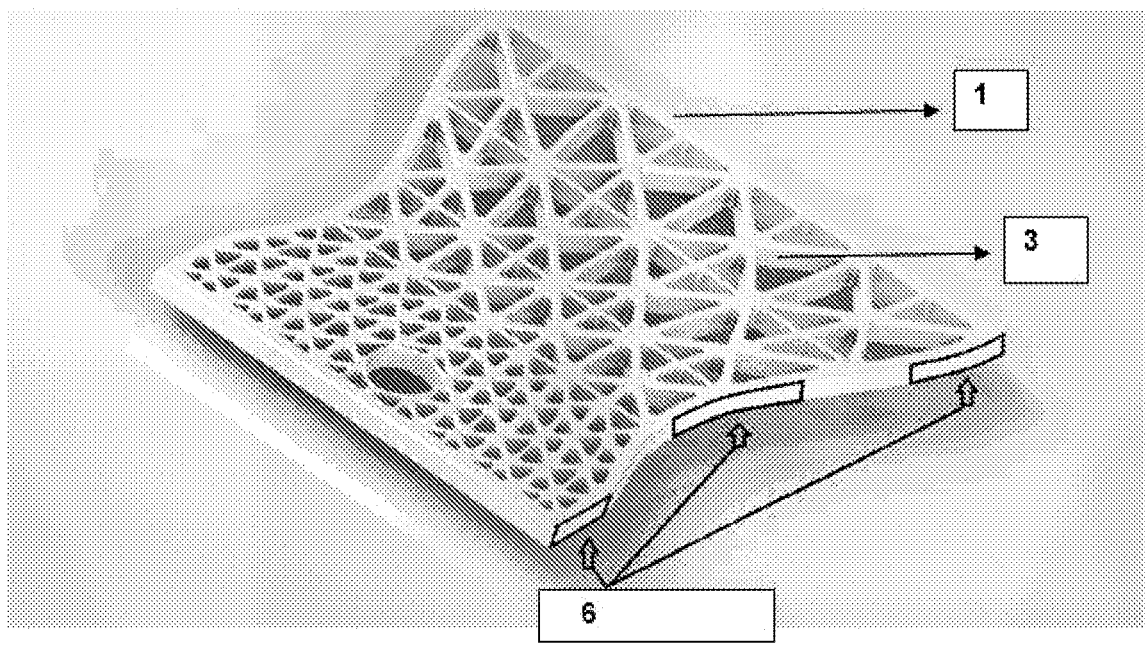
FIG. 3 illustrates the flexible cast member with a locking member provided on one periphery surface of the said flexible cast member, in accordance with an embodiment of the present subject matter.

In one implementation, the flexible cast (1) further comprises at least one locking member (6) as shown in FIG. 3 that can be provided on a periphery surface of said customizable cast member (1). The locking member (6) is adapted to secure said periphery surface to the other end when the customizable cast member may be wrapped around an injured body member. The locking member can be selected from, but not limited to, snap fit, Velcro™ or any combination thereof.

In one implementation, the flexible cast member (1) can be a flat unfolded geometry which can be wrapped over a fractured limb and the flexible cast member can be fixed with the locking means. This structure of the breathable orthopedic cast device gives more feasibility during application, less pain to the patient and faster application. The flat, unfolded design of the flexible cast member reduces the requirement of size variation.

In one implementation, as shown in FIG. 2, the flexible cast member (1) has a cavity or an inlet (5) to receive infusion material using external techniques. The flexible cast member (1) comprises hollow tubes (small and inflated) and is infused with infusion material.

Figure 6:
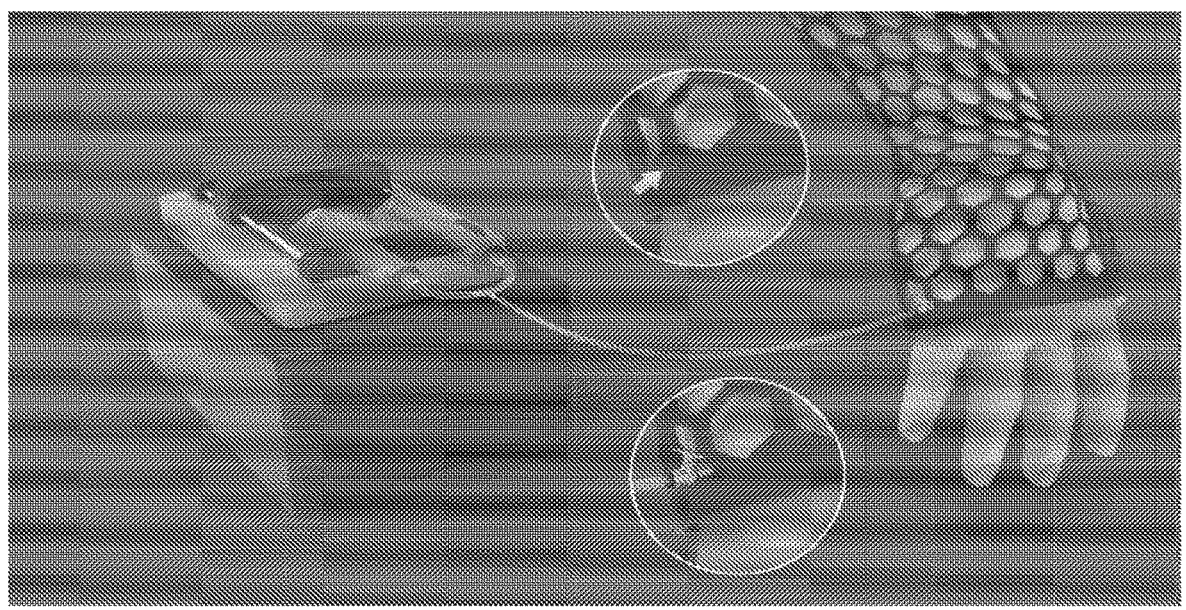
FIG. 6 illustrates application of an infusion material to the flexible cast member, in accordance with another embodiment of the present subject matter.

In one implementation, the infusion material can be pre-injected into the cavities of the hollow tubes of the flexible cast member (1) before application to a fractured limb. This may remove the need for an infusion assembly in the cast member as shown in FIG. 6. Due to the removal of the Infusing assembly from the device, the application process and expected time to apply has been reduced from 20 minutes to 10 minutes. Curing of the infusion material can be initiated externally using a specific technique. This can reduce the total application time of the breathable orthopedic cast device around the fractured limb from 20 minutes to 10 minutes. The pre-injected material may be a visible light curable epoxy resin which can be cured when exposed natural day light.

Figure 4:
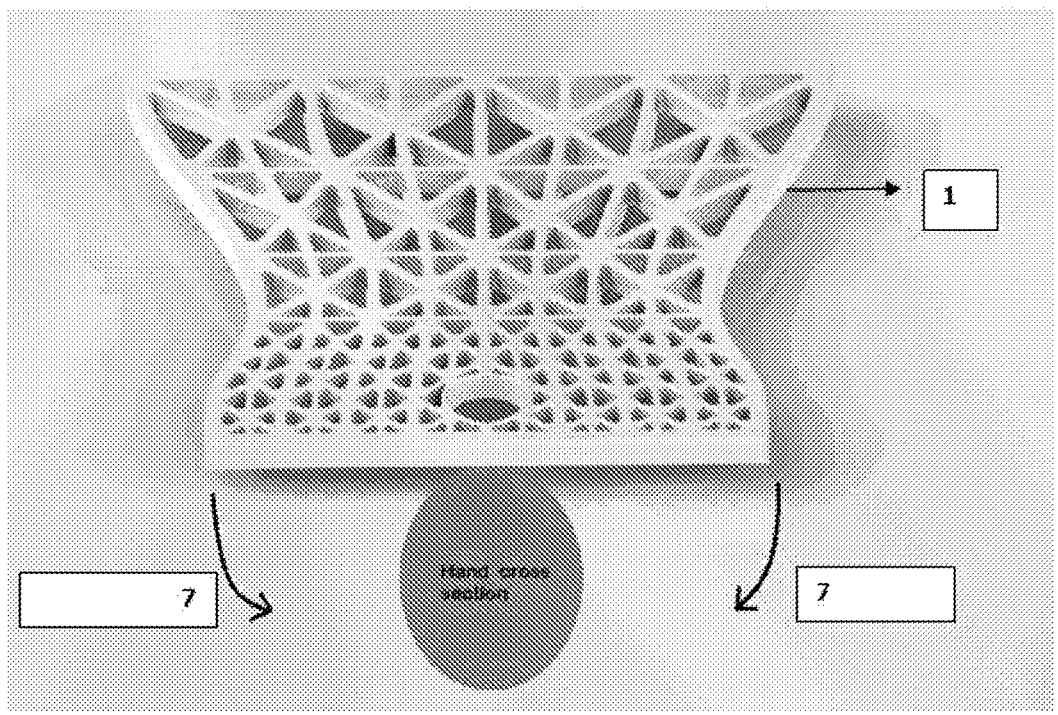
FIG. 4 illustrates the flexible cast member being wrappable around a fracture site, in accordance with an embodiment of the present subject matter.

In one implementation, as shown in FIG. 4, the flexible cast member is capable of being wrapped in a particular direction (7) around a fracture site and gets securely locked by engaging the locking member (6) as illustrated in FIG. 3.

Figure 5:
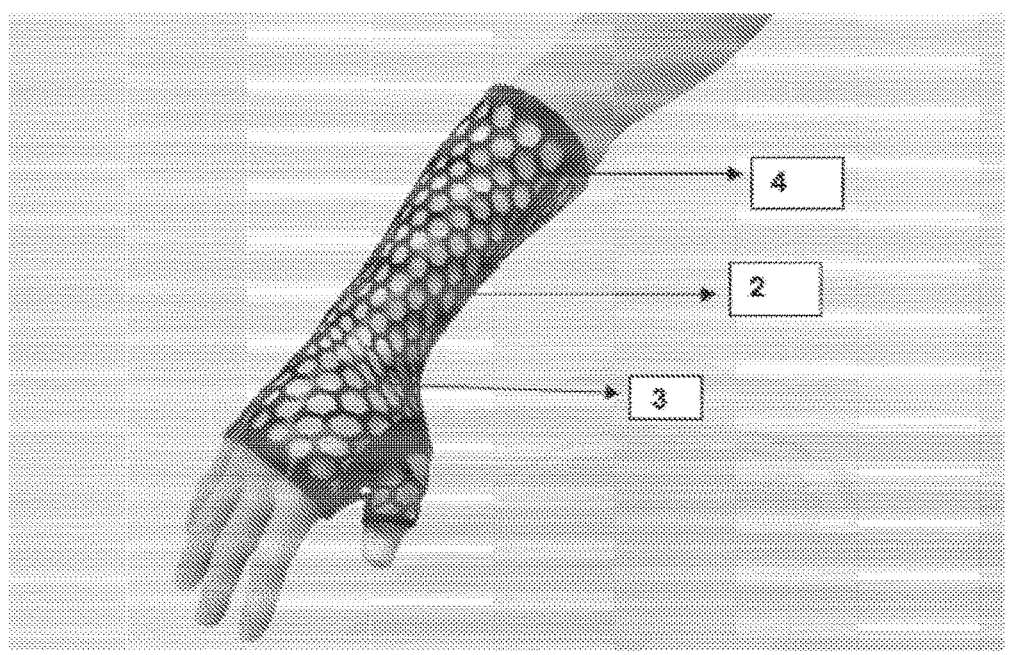
FIG. 5 illustrates the flexible cast member after application to an individual's limb, in accordance with an embodiment of the present subject matter.
Figure 7:
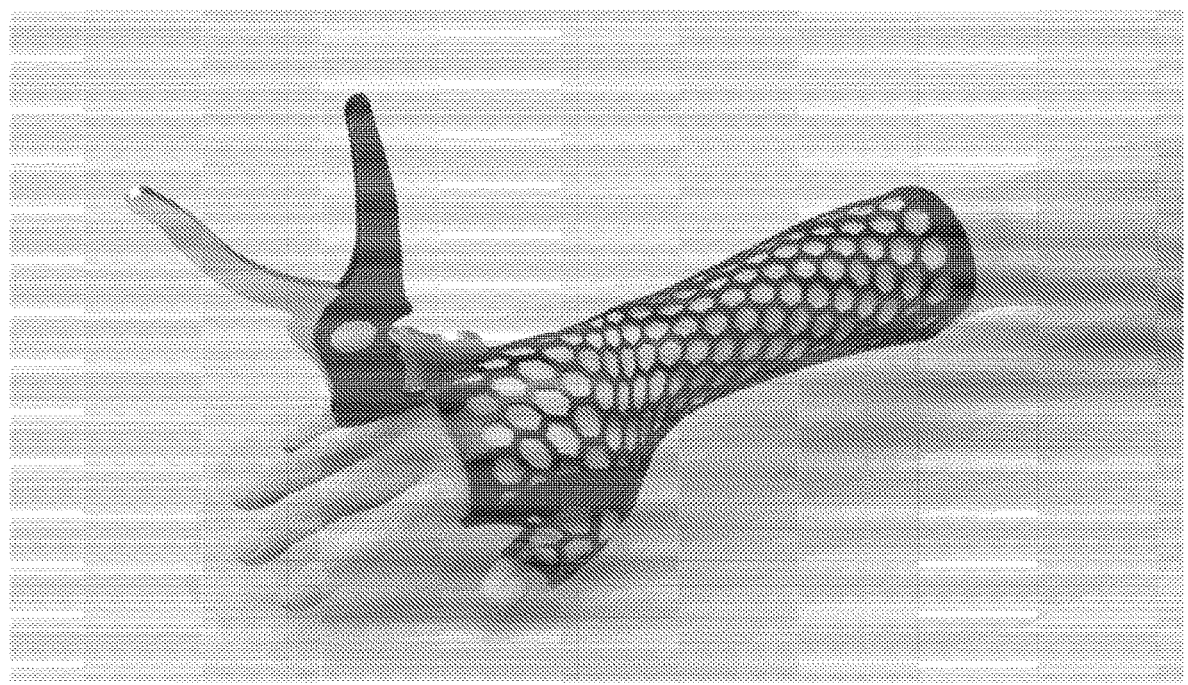
FIG. 7 illustrates a cast cutter to cut the flexible cast member, in accordance with an embodiment of the present subject matter.

In another implementation, as shown in FIG. 5, the flexible cast member (2) is shown after application to an individual's limb wherein the flexible cast member can be used like a Flexible Glove. The Flexible Glove like structure of the cast device (2) can be rolled down initially and then while wearing on the limb it is rolled up on the selected limb. The glove like structure is identical to rubber gloves comprising and interlinked network of hollow tubules (4) which may be worn on the fractured limb and the infusion material may be post-injected at the time of application for hardening the cast to immobilize the limb. The infusion/injection of a material is required after wearing the flexible cast as shown in FIG. 6. The flexible Glove like structure is rolled down initially and then while wearing on the limb, it is rolled up on the selected limb. The cavity/hole provided in said flexible cast member facilitates infusion material to be infused inside the cast member after application to the fractured limb. The Flexible Glove like structure can easily cut by means of a cutting tool as shown in FIG. 7. The cutting tool can be a hand operated device that works without electricity. The tool has a hinge and blunt blades facing inside for safe cutting. The cutter can also be mechanically powered as it requires no external power source and is safe even in unskilled hands.

In all implementation, the size of the flexible cast member (1 & 2) can be customized according to the patient's limb size. The cast member can be made up of a material selected from a group of a flexible/elastic material that may include but is not limited to a silicon rubber, latex rubber, synthetic rubber or any combination thereof to provide adequate elasticity and flexibility as required by the cast member. The materials are stretchable and provide the ability to accommodate external features of a patient's limb. The mesh like structure (3) of the flexible cast member (1 & 2) enables doctors or technicians to monitor normal circulation or swelling around the fracture site.

In all the implementations, the infusion material can be selected from a group of low viscosity epoxy material that includes epoxy resins, polymers, acrylate fillers and activators, polyurethane or any combination thereof.

In all the implementations, the curing of the infusion material is done using a curing technique that may be selected from any composite material curing technique that may include but is not limited to, thermal curing, ultra violet curing, visible light curing electromagnetic or electron curing and the like. In the implementation of the present invention, light curable composite epoxy resin can used as an infusion material. Therefore, the property of light curing techniques gives freedom to cure material by exposing it to light and plain epoxy is mixed with filler material such as nanofibers to increase the strength of the cured material. The curing techniques have to be carried out under strict medical supervision if used in orthopedic practices.

In all implementations, the breathable orthopedic cast device for immobilizing and stabilizing comprises the following components:
1. Customizable cast (1 or 2);
2. Hardening or infusion material.

Customizable Cast:

In one implementation, the customizable cast member (1) may be a flat unfolded geometry which can be wrapped over a fractured limb and may be fixed with specially designed locks. The customizable cast member may be made of a material selected from a group of a flexible material that includes a silicon rubber, latex rubber, synthetic rubber or any combination thereof. The customizable cast member may be customized into 4-5 sizes according to anthropometric data. The Cast has different small geometry's inspired from nature to give the strongest structure. Cast shape may vary according to fracture site and the purpose of application that may include but is not limited to short arm cast, full arm cast, barrel cast for both limbs, Spica, neck collar. On choosing an appropriate size, the cast will take shape according to contours of patient's limb. The cast member (1) may be provided with a locking member (6) to secure the cast member when it is wrapped around a fractured limb.

In another implementation of the invention, the flexible cast (2) may be identical to rubber gloves that comprises an interlinked network of hollow tubules (4) which may be worn on the fractured limb. The flexible cast (2) can be cut by means of a cutting tool as shown in FIG. 7 during removal.

In both the implementations, the cast member may be in the form of a mesh structure (3) made of hollow tubes (small and inflated) interlinked with each other such as to form a mesh like structure (3) forming the customizable cast. The hollow tubes (4) of the cast may be pre-infused or post-infused with the infusion material. The cast comprises an opening/hole through which the infusion material is infused in the cast.

Infusion Material/Hardening Material:

In one implementation, the infusion material can be a monomer material which is selected to give adequate strengthening for immobilization. Material will be provided as two premix forms which will be mixed by an infusing system and infused into the flexible cast. Polymerization may start within 5-10 minutes and can give basic hardening strength within 15 minutes. On complete polymerization, the infusion material may strengthen the cast member to give strength. The infusion material can be pre-infused or post-infused into channels of gloves from an infusion port. Infusion material is fast curing, low viscosity epoxy material which will be provided in the form of a two cartridge or premixed cartridge with flexible cast packing. Infusion may take place by infusion assembly as shown in FIG. 6, which works like a syringe pump, is mechanical or electrically powered and has tubes to connect with an infusion port. Infusion can be done in a reduced fracture position and maintained for 10-15 minutes after infusion. The flexible cast thereafter can achieve capable enough strength for stabilization of bone or damaged tendons. The mesh like structure of the cast provides breathability and visibility to skin under the cast. No padding is used in the cast so the flexible cast member can be washed and cleaned whenever required.

The infusion material used in the present invention can be any material which has lower viscosity, which is skin friendly so that it does not harm even if it gets in contact with skin accidentally and which is able to be transformed into hard material within 10 minutes after the infusion.

In one implementation, the breathable orthopedic cast device can be supplied to a hospital as a flat, elastic and highly flexible structure (1) in a specialized design and having a hole for a finger or any particular anatomical bone mark, other holes for breathability and a lock on the surface. The whole device can be covered by a dark nontransparent polythene layer which can later be removed after application. The purpose of the polythene layer is to block sunlight to the epoxy material which may get cured if exposed to sunlight for prolonged periods. In the implementation, any material which blocks sunlight and can be removed when required, is suitable for this purpose.

According to another implementation of the present invention, the flexible cast (2) is made like a rubber pouch in the shape of hand glove with multiple holes. A cast made of the rubber can be adapted to the shape and size of the limb and enables the hardening material from being exposed to skin. Hardening material is filled in the cavity.

In the present invention, the breathable cast device (1) can be applied by wrapping over the fractured body part and securing the lock after keeping proper tension over the device. The breathable flexible cast (2) device can also be worn like a glove. Fractured bone can be aligned into normal anatomical position and curing initiated by unwrapping the dark polythene layer. Light curable material can be pre-infused or post-infused into the hollow tubes (4) and cured within 5 minutes after unwrapping the polythene layer. In some case artificial light may be required when natural light is not adequate at the time i.e. night or place i.e. closed room of the application. The time of curing can be reduced from 10 minutes to 5-7 minutes. For removal of the device, either the locking means can be released or the breathable cast device (2) can be cut by mean of a cutting tool.

The present invention provides a cost effective and highly efficient casting system/assembly. The breathable cast device has the following advantageous technical features:

lighter in weight;

breathable: due to the mesh/network structure, the device facilitates air passage to the skin and prevents sweating;

washable;

able to be customized according to the need of an individual patient;

is capable of maintaining a uniform pressure throughout the covered area and allows a user to view the skin to watch for swelling of the covered skin;

The complete cast system/assembly works in low resource settings;

Supports dry curing, that is, the cast member doesn't require water for curing;

Supports programmable Time to operate, that is, control over curing process;

Application of the breathable orthopedic cast device can be extended to muscle or tendon sprains, joint injury, Scoliosis or other conditions which require short-term or long term immobilization.

There is no need for padding material or a padding layer because the flexible part of the cast is made up of skin safe material.

There will be uniform pressure because the flexible part of the cast adapts to the shape and size of a limb.

The elastic material, i.e., silicon rubber, itself provides cushioning because of its compressibility Although implementations for a breathable and customized cast for immobilization of a fractured limb have been described in language specific to structural features and/or methods, it is to be understood that the appended claims are not necessarily limited to the specific features or methods described. Rather, the specific features and methods are disclosed as examples of implementations for a breathable and customized cast for immobilization of fractured limbs.

The invention claimed is:

1. A breathable orthopedic cast device comprising:

a cast member consisting of a single layer cavity sheet structure of small and inflated hollow tubes interlinked and in fluid communication with each other to form a mesh structure; wherein said hollow tubes are adapted to be in direct contact with skin of a selected limb of a user during use of the orthopedic cast device and said orthopedic cast device is devoid of fabric or cushioning material intervening between said hollow tubes and the skin of the selected limb during use, said cast member adapted to be injected with at least one infusion material in said hollow tubes, wherein said at least one infusion material is configured to harden in said hollow tubes when said hollow tubes are in direct contact with the skin of the selected limb in use, said at least one infusion material being selected from a group consisting of polyepoxide material that includes epoxy resins, acrylate fillers and activators, polymer or any combination thereof, wherein said at least one infusion material is adapted to be hardened or cured by application of external UV light or natural light for at least 10 minutes;

wherein said cast member is formed of flexible material consisting of silicone rubber, latex rubber, synthetic rubber or any combination thereof;

wherein said cast member is configured to be in a rolled configuration initially and then unrolled onto the selected limb during use;

wherein said cast member has a flat unfolded geometry wherein said mesh structure is preshaped and configured to conform to a portion of the selected limb; and said orthopedic cast device further comprising at least one locking member provided on at least one periphery surface of said cast member, to provide means for attachment and removal of said cast member;

wherein said at least one locking member is a hook and loop or snap fit attachment member adapted to secure said at least one periphery surface to a second end when said cast member is applied to the selected limb, and provides adjustment in said cast member to conform to the selected limb.

2. The breathable orthopedic cast device of claim 1, wherein said cast member has a shape configured for corresponding to contours of the portion of the selected limb and wherein the device is a glove wearable over the portion of the selected limb.

3. The breathable orthopedic cast device of claim 1, wherein said cast member is configured to be adjusted according to a contour of the selected limb of the user during hardening or curing of said cast member, due to an elasticity and flexibility of silicone rubber used for said cast member and non-rigid locking provided by said hook and loop or snap fit attachment member used as the at least one locking member for said cast member.

* * * * *